US011566264B2

(12) United States Patent
Sarraf

(10) Patent No.: US 11,566,264 B2
(45) Date of Patent: Jan. 31, 2023

(54) PROCESS FOR OBTAINING A CEMENTITIOUS MINERAL SUBSTANCE

(71) Applicant: SOLETANCHE FREYSSINET, Rueil Malmaison (FR)

(72) Inventor: Riad Sarraf, Querqueville (FR)

(73) Assignee: SOLETANCHE FREYSSINET, Rueil Malmaison (FR)

( * ) Notice: Subject to any disclaimer, the term of this patent is extended or adjusted under 35 U.S.C. 154(b) by 256 days.

(21) Appl. No.: 15/495,595

(22) Filed: Apr. 24, 2017

(65) Prior Publication Data

US 2017/0306357 A1 Oct. 26, 2017

(30) Foreign Application Priority Data

Apr. 25, 2016 (FR) ..................................... 16 53614

(51) Int. Cl.
| | |
|---|---|
| *C12P 1/04* | (2006.01) |
| *C12P 3/00* | (2006.01) |
| *C04B 28/10* | (2006.01) |
| *C12N 1/20* | (2006.01) |
| *C04B 111/72* | (2006.01) |

(52) U.S. Cl.
CPC ................ *C12P 1/04* (2013.01); *C04B 28/10* (2013.01); *C12N 1/20* (2013.01); *C12P 3/00* (2013.01); *C04B 2111/72* (2013.01); *Y02P 40/18* (2015.11)

(58) Field of Classification Search
CPC ... C12P 1/04; C12P 3/00; C04B 28/10; C04B 2111/72; C12N 1/20; Y02P 40/18
USPC ....................................................... 435/170
See application file for complete search history.

(56) References Cited

FOREIGN PATENT DOCUMENTS

| FR | 2 430 727 A1 | 2/1980 |
|---|---|---|
| FR | 2 723 080 A1 | 2/1996 |
| FR | 2 948 224 A1 | 1/2011 |
| GB | 2 026 028 B | 1/1980 |
| KR | 100840602 * | 6/2008 |
| WO | 95/29250 A1 | 11/1995 |
| WO | WO 1995/29250 * | 11/1995 |
| WO | WO1995/29250 * | 11/1995 |

OTHER PUBLICATIONS

Suarez et al., Assessment of the Metabolism of Different Strains of Bacillus megaterium, Brazilian Archives of Biology and Technology, vol. 55, n. 4, pp. 485-490, Jul.-Aug. 2012.*
JP 2011032427 (English Translation).*
Chen et al., Isolation and identification of lactic acid bacteria from soil using an enrichment procedure, Letters in Applied Microbiology 2005, 40, 195-200.*
Dhami et al., Bacillus megaterium mediated mineralization of calcium carbonate as biogenic surface treatment of green building materials, World J Microbiol Biotechnol (Jun. 2013).*
Leme et al., The Role of Sucrose in Cariogenic Dental Biofilm Formation—New Insight, Journal of Dental Research, vol. 85, Issue 10, (2006), pp. 878-887.*
Verywellhealth, Dental Health, The Importance of Tooth Enamel, Accessed Sep. 14, 2020, Available online at: www.verywellhealth.com/enamel-definition-of-enamel-1059421.*
Varenyam Achal et al., "Improved strength and durability of fly ash-amended concrete by microbial calcite precipitation", Ecological Engineering, Elsevier, Amsterdam, NL, vol. 37, No. 4, Nov. 7, 2010, pp. 554-559, XP028146959.
Tingting Zhu et al, "Potential application of biomineralization by Synechococcus PCC8806 for concrete restoration", Ecological Engineering, vol. 82, Sep. 1, 2015, pp. 459-468, XP055329067.
Le Metayer-Levrel G et al, "Applications of bacterial carbonatogenesis to the protection and regeneration of limestones in buildings and historic patrimony", Sedimentary Geology, Elsevier, Amsterdam, NL, vol. 126, Jan. 1, 1999, pp. 25-34, XP002448927.
B.A. Shenderov, Medical microbial ecology and functional nutrition. Volume III: Probiotics and functional nutrition. Moscow: Grant Publishing house, 2001, p. 51.
L V. Solovieva et al., "Study of the biological properties of new strains of the genus Lactobacillus", Bulletin of N. I. Lobachevsky University in Nizhniy Novgorod, 2010, v. 2, No. 2, pp. 462-468, especially abstract, pp. 463-468, fig. 1, in Russian with English abstract.
I. V. Solovieva et al., "Study of the biological properties of new strains of the genus Lactobacillus", Bulletin of N. 1. Lobachevsky University in Nizhniy Novgorod, 2010, v. 2, No. 2, pp. 462-468, especially abstract, pp. 463-468, fig. 1 (only English translation provided).
B. M. Borah et al., "Lactic acid bacterial extract as a biogenic mineral growth modifier", Journal of Crystal Growth, vol. 311, Issue 9, Apr. 15, 2009, pp. 2664-2672, full document.
E. Rossland et al., "Inhibition of Bacillus cereus by strains of *Lactobacillus* and *Lactococcus* in milk", Int. J. Food Microbiol, Dec. 31, 2003, 89 (2-3): 205-212, Https://doi.org/10.1016/s0168-1605(03)00149-I, Retrieved May 20, 2021, see abstract, tables 2, 3, 4.

(Continued)

*Primary Examiner* — Jennifer M. H. Tichy
(74) *Attorney, Agent, or Firm* — Dentons US LLP

(57) ABSTRACT

The invention relates to a method for obtaining a mineral substance from a base comprising mineral matter, the method comprising obtaining the base comprising a predetermined quantity of the mineral matter synthesised by a living structure or a portion of the latter,
characterised in that obtaining the base comprises providing the living structure and providing at least one lactic acid microorganism suitable for symbiosis with the living structure for the synthesis of the mineral matter of the mineral substance.
The invention also relates to a mineralising composition comprising a living structure, a lactic acid microorganism, a nutritive substance; the mineral substance used in the method; and the use of a combination of a living structure and a lactic acid microorganism in symbiosis with each other as a mineralising agent in a self-regenerating material.

8 Claims, 3 Drawing Sheets

(56) References Cited

OTHER PUBLICATIONS

F. Djadouni et al., "Antimicrobial Activity of Lactic Acid Bacteria and the Spectrum of their Biopeptides Against Spoiling Germs in Foods", Braz. Biol. Technol., vol. 55 No. 3 Curitiba May/Jun. 2012, https://doi.org/10.1590/S1516-89132012000300015, Retrieved May 20, 2021, see Table 1.

F. Minervini et al., "Lactic Acid Bacteria in Durum Wheat Flour Are Endophytic Components of the Plant during Its Entire Life Cycle", Applied and Environmental Microbiology, Sep. 2015, 81 (19) 6736-6748.https: //doi.orq/10.1128/AEM.01852-15, Retrieved May 20, 2021, see abstract.

Y.-S. Chen et al., "Isolation and identification of lactic acid bacteria from soil using an enrichment procedure", Lett. Appl. Microbiol. 2005,40 (3): 195-200, https://doi.org/10-1111/j.1472-765X.2005.01653.x Retrieved May 20, 2021, see abstract, table 2, p. 195, left col. first paragraph.

B.A. Shenderov, Medical microbial ecology and functional nutrition. Volume III: Probiotics and functional nutrition. Moscow: Grant Publishing house, 2001, p. 51. (Automated English translation for p. 51 provided.).

\* cited by examiner

PROCESS FOR OBTAINING A CEMENTITIOUS MINERAL SUBSTANCE

This application claims priority to French Patent Application No. 16 53614 filed on Apr. 25, 2016 in France, which is hereby incorporated by reference in its entirety for all purposes as if fully set forth herein.

TECHNICAL FIELD

The present invention relates to the field of cement mineral substances and the methods for obtaining them biologically. The present invention also relates to the field of self-regenerating materials comprising a cement mineral substance and their manufacturing methods.

PRIOR ART

Methods for obtaining mineral substances using a biological method for producing mineral matter and using mineral substrates are known, such as those described in documents FR2723080 and FR2644475. These types of mineral matter are of natural or artificial origin, or a portion of these types of matter is of natural origin and another portion is of artificial origin.

The term "mineral" should be understood here in the broad sense and means "including in its composition at least one mineral, in particular a carbonate mineral," that is to say, generally solid matter defined by its chemical composition and the ordered arrangement of its atoms. The chemical composition of a mineral consists for the most part, substantially, or even exclusively of elements other than carbon.

The term "of artificial origin" means "that is synthesised by the action of man," as opposed to "of natural origin," which means "that is synthesised in nature."

These mineral substances thus created can be used to replace and/or repair or complement mineral substrates such as stone, in particular limestone, dolomitic rock or gypsum rock, while having a structure, appearance and texture close or similar to those of these substrates.

The known methods, in particular those described in documents FR 2723080 and EP 0708836, comprise in particular the steps of:
a) preparing a base comprising a predetermined quantity of mineral matter synthesised by at least one living structure or at least a portion of a living structure, the living structure belonging to the plant, animal or microorganism kingdom; and
b) treating said base in such a way as to transform it into a deactivated mineral substance having a predefined texture according to the extemporaneous use for which it is intended, for example for its use as a raw material for immobilising waste via cementation, also called intake filler ("charge d'apport" in French).

In these documents, the term "base" designates either the mineral matter alone or the combination of the mineral matter with a base substrate enabling its development. The mineral matter can be, for example, calcium oxalate, calcium carbonate, silica, etc.

In these documents, the expression "living structure" designates any cellular structure or a structure of cellular origin (plant, animal or microorganism), living and/or resulting from life and/or from the compounds of biological origin, crystallised or not, such as enzymes, hormones, proteins, DNA; these living structures being mineralising, mineralised or mineralisable (or petrifying), that is to say, capable of synthesising, in nature or artificially, mineral matter (patents FR 2723080 and EP 0708836).

These known methods, although satisfying in principle, need to be improved in certain cases.

PRESENTATION OF THE INVENTION

Thus, the present invention provides a method for obtaining a mineral substance from a base comprising mineral matter, the method including obtaining the base comprising a predetermined quantity of the mineral matter synthesised by a living structure or a portion of the latter, characterised in that obtaining the base includes providing the living structure and providing at least one lactic acid microorganism suitable for symbiosis with the living structure for the synthesis of the mineral matter of the mineral substance.

The addition of a lactic acid microorganism enables the mineralisation process of the mineral substances thus created (i.e. production of the mineral matter contained in the mineral substances) to be accelerated, the minerality of these substances to be improved, and these substances to be diversified.

Obtaining the base can further include providing a nutritive substance, preferably glycerol carbonate and/or derivatives of glycerol carbonate.

The living structure and the lactic acid microorganism can be provided together in order to form a biological complex.

The lactic acid microorganism can be provided first, and then the living structure.

Obtaining the base can further include providing a base substrate suitable for the development of the living structure and/or of the lactic acid microorganism and bringing the base substrate in contact with the living structure and the lactic acid microorganism.

The method can further include cleaning of the surfaces of the base substrate in contact with the lactic acid microorganism by this latter; synthesising the mineral matter by the living structure, cleaning and synthesising can take place simultaneously or successively in this order.

The method can further include deactivating the base to obtain a deactivated mineral substance. The invention also provides a mineralising composition comprising:
a. a living structure or at least a portion of a living structure;
b. at least one lactic acid microorganism; and
c. a nutritive substance.

This composition can further be formulated for extemporaneous use.

The invention also provides a mineral substance comprising:
a.—a living structure or at least a portion thereof;
b.—at least one lactic acid microorganism; and
c.—mineral matter synthesised by the living structure or the portion thereof.

This mineral substance may be obtained in particular using the method described above.

The mineral substance can further comprise a base substrate suitable for the proliferation of the living structure and/or of the lactic acid microorganism.

The mineral matter, and optionally the base substrate, can be in a porous form, with pores, opening outside of the mineral substance, in which the living structure and the lactic acid microorganism are present.

The living structure and/or the lactic acid microorganism can be deactivated.

Finally, more generally, the present invention provides the use of a combination of a living structure and a lactic acid microorganism in symbiosis with each other as a mineralising agent in a self-regenerating material, the lactic acid microorganism being suitable for secreting lactic acid; and that of the mineralising composition or of the mineral substance described above as a repairing agent in a self-regenerating material.

DRAWINGS

Other purposes, features and advantages will become apparent when reading the following description with reference to the exemplary and non-limiting drawings, among which:

DETAILED DESCRIPTION

Method for Obtaining a Mineral Substance

Figure 1:
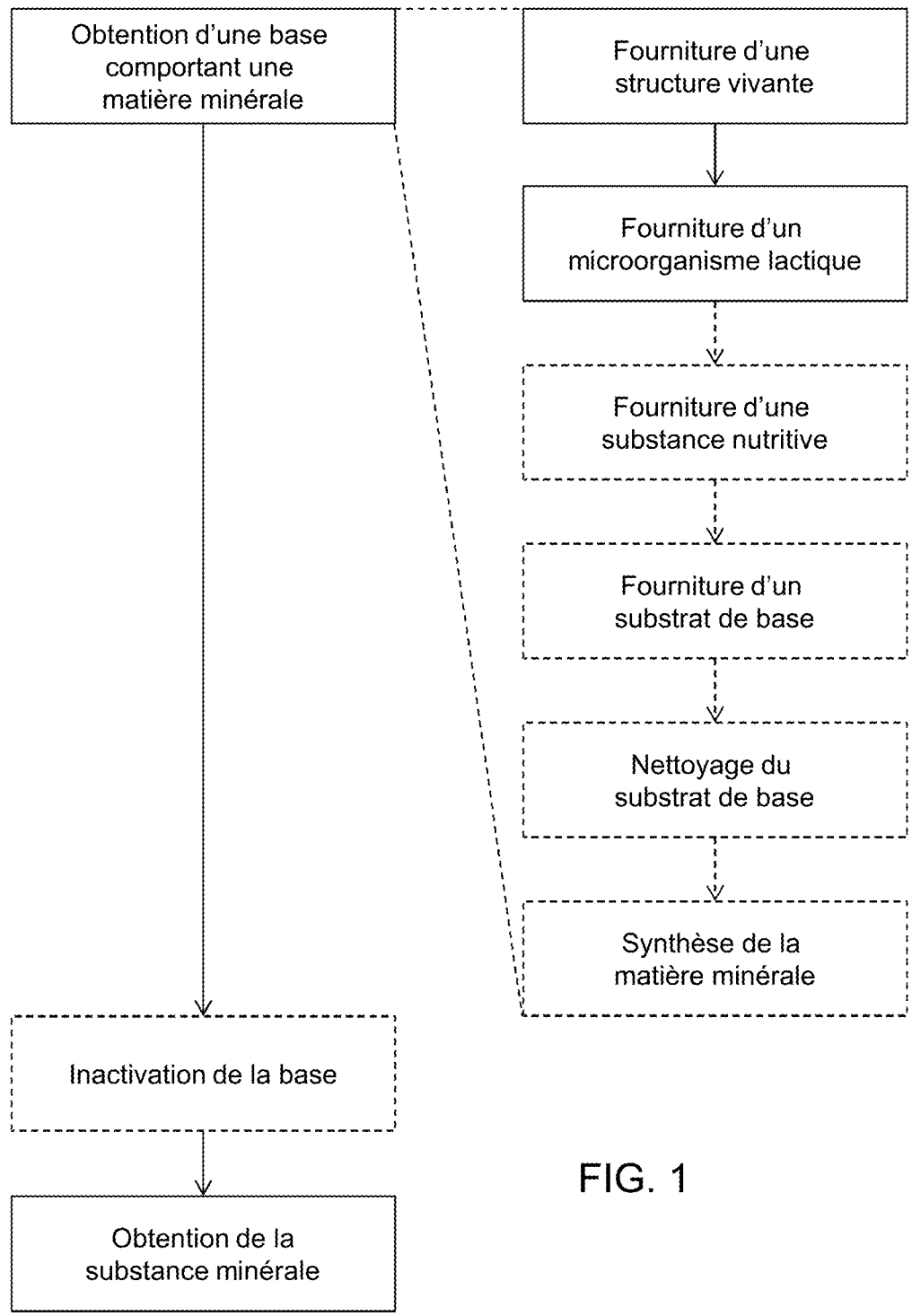
FIG. 1 is a flowchart showing the various steps of the method according to the invention.

A method for obtaining a mineral substance comprising mineral matter is described below with reference to FIG. 1.

Here, the term "substance" designates a material or a composition.

This method involves obtaining a base comprising a predetermined quantity of the mineral matter synthesised by a living structure or a portion of the latter, and transforming the base into the mineral substance. The mineral matter comprises in particular limestone or calcium. Hereinafter, reference will only be made to the living structure to facilitate the reading of the present disclosure, but the occurrences of these terms should be understood as also including the embodiments in which the living structure is replaced by a portion thereof, including for the other aspects of the invention.

Obtaining the base includes providing the living structure and providing at least one lactic acid microorganism suitable for symbiosis with the living structure for the synthesis of the mineral substance.

The term "carbonate mineral" should be understood here in the broad sense and means "including in its composition at least one mineral," that is to say, generally solid matter defined by its chemical composition and the ordered arrangement of its atoms. The chemical composition of a mineral consists for the most part, substantially, or even exclusively of elements other than carbon other than in carbonate.

Here, the term "base" designates either mineral matter alone or the combination of mineral matter with a base substrate enabling its development. During its development on the base substrate, the mineral matter at least partially replaces the base substrate.

The mineral matter can be, for example, calcite, oxalates such as calcium oxalate, carbonates (in particular biocarbonates and oligocarbonates) such as calcium carbonate, silica, silico-carbonates, etc. FIGS. 2 to 8 show various types of obtainable mineral matter.

In the context of the present invention, the term "symbiosis" designates a close, durable association between two organisms (here, the living structure and the lactic acid microorganism; the two can be qualified as symbionts). Thus, the cases of parasitic relationships, i.e. in which one of the two organisms gains an advantage while the other suffers the costs, are not included.

Consequently, whether while obtaining the base or when using the mineral substance, the lactic acid microorganism, during fermentation, produces lactic acid and carbon dioxide that act as a mineral precursor for the synthesis of the mineral matter by the living structure, in particular via organic mineralisation-carbonation, which is a hybrid mineralisation. The mineral matter thus obtained via hybrid mineralisation becomes reinforced in comparison with mineral matter obtained without the addition of a lactic acid microorganism. Indeed, the mineral matter, which is both organic and mineral at molecular scale, is stable because of its insolubility in water. Moreover, the mineral matter has an open porosity.

In the context of the present invention, the wording "living structure" designates any structure that is cellular or of cellular origin (from the plant kingdom, the animal kingdom, the kingdom Archaea, the kingdom Bacteria, the kingdom Protista or the kingdom Fungi), living and/or resulting from life and/or from the compounds of biological origin, crystallised or not, such as enzymes, hormones, proteins, DNA; these living structures being mineralising (capable of producing mineral matter), mineralised (at least a portion of which has become mineral matter) or mineralisable (or petrifying, i.e. at least a portion of which is capable of becoming mineral matter). Thus, they are suitable for synthesising or producing, in nature or artificially, mineral matter.

The living structure is preferably a calcified and/or calcifying (i.e. that produces a mineral comprising calcium and/or magnesium) living structure.

The living structure can be provided via culture or collection (in nature).

If it is cultured, the conditions (for example time and culture medium) of the culture thereof are chosen to enable synthesis of the mineral matter. Preferably, the living structure is cultivated until it reaches its exponential growth phase. The exponential growth phase can be verified, for example, through optical density.

If it is the result of collection or harvesting, the living structure is then incorporated into the base.

In one embodiment, the living structure is one or more calcifying bacteria capable of mineralisation-carbonation according, for example, to the method described in documents FR2723080 and EP0708836. Examples of such bacteria are chosen from the genera *Bacillus* and *Pseudomonas*.

"Lactic acid microorganism" means a living microorganism (such as yeast, bacteria or viruses) capable of associating via symbiosis with the living structure and/or with each other in order to live and develop and capable of lactic fermentation, that is to say, capable of producing lactic acid under anaerobic conditions and in the presence of carbohydrates.

If there is only a single lactic acid microorganism, it is capable of symbiosis with the living structure. However, if there is a plurality of lactic acid microorganisms, it is not necessary for all of the lactic acid microorganisms to be capable of symbiosis with the living structure; one lactic acid microorganism with such a property is enough. The lactic acid microorganisms not capable of symbiosis with the living structure are at least capable of symbiosis with each other.

These lactic acid microorganisms naturally act in symbiosis and have properties that promote the synthesis of minerals, in particular carbonate minerals. Thus, they improve the medium in which the living structure synthesises mineral matter by producing carbon dioxide through fermentation and lactic acid. The actions of the lactic acid microorganisms are, in particular:
   a. lowering the pH of the medium in which the living structure synthesises the mineral matter;
   b. enzymatic digestion of the organic matter, including the ligneous and cellulosic fibres, that is favourable to the anchoring and grafting of the mineral matter synthesised by the living structure;
   c. moving the calcium carbonate equilibrium towards the production of carbon dioxide through the fermentation induced by the lactic acid microorganisms, which is favourable to the synthesis of the carbonate mineral matter by the living structure; and
   d. cleaning the surfaces of a base substrate in preparation for the anchoring of the mineral matter synthesised by the living structure.

In order to facilitate the reading of the present disclosure, reference will only be made to a single lactic acid microorganism. However, this should be understood as including the embodiments in which more than one lactic acid microorganism is used, at least one of which is capable of symbiosis with the living structure, including for the other objects of the invention.

The lactic acid microorganism can be chosen from the group consisting of: the family Aerococcaceae, the family Bifidobacteriaceae, the family Carnobacteriaceae, the family Enterococcaceae, the family Lactobacillaceae, the family Leuconostocaceae, the family Saccharomycetaceae, the family Sporolactobacillaceae and the family Streptococcaceae.

Preferably, the lactic acid microorganism is chosen from the group consisting of: the family Bifidobacteriaceae, the family Lactobacillaceae, the family Saccharomycetaceae and the family Streptococcaceae.

Again preferably, the lactic acid microorganism is chosen from the group consisting of: the family Bifidobacteriaceae, the family Enterococcaceae, the family Lactobacillaceae, the family Leuconostocaceae, the family Saccharomycetaceae and the family Streptococcaceae.

In the family Bifidobacteriaceae, *Bifidobacterium* sp., in particular *B. lactis*, *B. breve* and *B. bifidum*, can be cited.

In the family Enterococcaceae, *Tetragenococcus* sp., in particular *T. halophilus, T. muriaticus, T. solitarius, T. koreensis* and *T. osmophilus*, can be cited.

In the family Lactobacillaceae, *Lactobacillus* sp. and *Pediococcus* sp can be cited.

In the family Leuconostocaceae, *Leuconostoc* sp. and *Oenococcus* sp., in particular *L. mesenteroides* and *O. oeni*, can be cited.

In the family Saccharomycetaceae, *Saccharomyces* sp., in particular *S. cerevisiae* and *S. boulardii*, can be cited.

In the family Streptococcaceae, *Lactococcus* sp. and *Streptococcus* sp., in particular *L. lactis* (formerly *S. lactis*), can be cited.

Obtaining the base can further include providing a nutritive substance for the living structure and/or the lactic acid microorganism. This nutritive substance can in particular be chosen from glycerol carbonate, at least one derivative of carbonate, or a mixture thereof. The derivative of glycerol can be, for example, a glycerol ester.

The nutritive substance enables the living structure and/or the lactic acid microorganism to be fed, and the latter produces lactic acid and carbon dioxide during fermentation, providing the living structure with sources of precursors of minerals in order to make the organic mineralisation-carbonation last.

The nutritive substance can be contained in a suitable culture medium known to a person skilled in the art and in which the living structure and/or the lactic acid microorganism is cultivated. The culture medium can be a simplified liquid medium, in particular chosen from:
   a. an aqueous mixture comprising 5 g of glucose and 10 g of fructose 10 g, in 1 L of distilled water;
   b. M.R.S. agar (de Man, Rogosa and Sharpe agar), a selective medium allowing subcultures; and
   c. an aqueous mixture consisting of 30 g of Sabouraud agar powder in 1 L of distilled water.

Preferably, the lactic acid microorganism is cultivated until it reaches its exponential growth phase. The exponential growth phase can be verified, for example, through optical density.

The living structure and the lactic acid microorganism can be provided together or not, for example the lactic acid microorganism is provided first, and then the living structure.

The living structure and the lactic acid microorganism together form a biological complex.

The biological complex traps the carbon dioxide present in the medium in complex biocarbonates that it produces and into which it incorporates proteins having a biological glue function. These complex biocarbonates are similar to natural mineral deposits and have, thanks to their silica content, increased hardness in comparison with the known silica and calcium minerals. Moreover, these complex biocarbonates have an appearance and crystallographic and physico-chemical characteristics close to natural mineral materials.

If the living structure and the lactic acid microorganism can be provided together, the culture of the living structure and that of the lactic acid microorganism can be carried out in the same culture medium, preferably until they reach their exponential growth phase.

In this case, the culture medium advantageously comprises urea and glycerol carbonate in order to promote the development of highly varied types of biological mineralisation and the constitution of biochemical mineralisation through organic carbonatation, creating hybrids that is both organic and mineral at molecular scale, that is to say, new materials that are very stable thanks to more extensive specific binding functions.

The concept of a biological complex can be perfectly well understood if the lactic acid microorganism and the living structure are provided together, but is not limited to this situation. Indeed, if the lactic acid microorganism and the living structure are not provided together, they still also form a biological complex having activities that are useful but in a deferred manner before, during the synthesis of the mineral matter and during the use of the mineral substance.

Obtaining the base can also include providing a base substrate suitable for the development of the living structure and/or the lactic acid microorganism and putting the base substrate in contact with the living structure and the lactic acid microorganism.

The term "base substrate" designates any matter or material on or in which the living structure and/or the lactic acid microorganism can develop.

The mineral base substrate can be stone, in particular limestone, dolomitic rock or gypsum rock. The base substrate can be a portion of an existing edifice or a construction material intended for constructing a building or a construction work.

In this case, the method can also include cleaning the surfaces of the base substrate in contact with the lactic acid microorganism by this microorganism and the synthesis of the mineral matter by the living structure, and the cleaning and the synthesis can take place simultaneously or successively in this order.

The method can further include the deactivation of the base in order to obtain a deactivated mineral substance. Here, the term "deactivated" means "devoid of any biological activity", such as a biomineralising or pathogenic microbiological activity.

The deactivation of the base can be achieved through deactivation of the lactic acid microorganism and/or the living structure, in particular after a sufficient quantity of mineral matter has been synthesised.

The deactivation of the lactic acid microorganism and/or of the living structure can be carried out by placing the former in dormancy for example by freezing, lyophilisation, cryodesiccation or desiccation. The dormancy state designates a state in which the lactic acid microorganism remains alive but in a lethargic state characterised by halted development, although the microorganism remains in communication with the environment outside of the deactivated mineral substance. The lactic acid microorganism and/or the living structure in the dormancy state can be revived. The use of the revivable forms of the lactic acid microorganism and of the living structure enables self-repairing cement materials to be obtained and opens the door to biological super-cements and petrifying agents having improved setting, hardness and elasticity.

Alternatively or in addition, the deactivation of the living structure can be carried out by the addition of at least one salt such as a salt chosen from the group consisting of magnesium oxide (MgO), magnesium sulphate ($MgSO_4$), phosphate ($H_3PO_4$), calcium chloride ($CaCl_2$), barium chloride ($BaCl_2$), sodium fluorosilicate ($Na_2SiF_6$), carbonate salt ($CO_3^{2-}$), sodium silicate ($Na_2SiO_3$) and mixtures thereof. The salt is advantageously in anhydrous form.

Alternatively or in addition, the deactivation of the living structure can include the irradiation of this structure due to outside radiological activity and/or a rise in the temperature to a temperature higher than the temperature which the living structure can tolerate. In the latter case, the living structure is dead and cannot be reactivated.

Alternatively or in addition, the method can further involve transforming the base in order to confer a texture onto the deactivated mineral substance that corresponds to the use for which it is intended. For example, transforming is mixing and/or fragmenting the base to obtain a homogenous biomass that is a mixture of the mineral matter with the living structure and the microorganism. Mixing and/or fragmenting are carried out at least partially simultaneously with one of the steps described above, and in particular the deactivation of the base. Fragmenting can be carried out, for example, by grinding. Mixing can be carried out using a mixer known to a person skilled in the art. Fragmenting and/or mixing enable the mineral matter to be obtained in powder form and/or granular cluster form.

Transforming can further include diluting the base, in particular in a liquid, preferably aqueous, such as a nutritive solution for the living structure and/or the lactic acid microorganism, in particular in order to achieve immobilisation.

The method can further include incorporating a cohesion agent into the base. The cohesion and/or texture agent can be chosen, for example, from the group consisting of calcium, magnesium, silicon, barium sodium, iron, manganese, collagen, mucopolysaccharide, a polycellulose compound, and the mixtures thereof; or to at least one out of the biomass, the medium, the material, the base and the mineral matter.

Deactivating the base and/or mixing and/or fragmenting can be carried out successively or simultaneously. Preferably, deactivating preferably goes with transforming the deactivated base.

The mineral substance can be, for example, a construction material, a reinforced soil. The construction material can be obtained from the recycling of a starting construction material or from the reparation of the latter.

The present method can be used for multiple applications, such as confined construction or outdoor construction, ground reinforcement, agriculture; and enables many uses that are little known or even unknown at present to be contemplated, such as the reuse of waste from construction materials, the renovation of artificial surfaces, self-reparation of mortars, the filling of microcracks, and soil induration.

Mineralising Composition

The invention also relates to a mineralising composition advantageously used to carry out the method described above. The composition comprises the living structure, the lactic acid microorganism and the nutritive substance as described above.

The mineralising composition can contain 25 to 98 wt. % living structure, and the preferred upper limits and lower limits of this interval can be: 30 wt. %, 70 wt. %, 80 wt. % and 95 wt. %. Thus, the quantity of the living structure can preferably be comprised in any interval having the upper and lower limits mentioned above, in particular: 25 to 70 wt. %, 30 to 70 wt. %, 80 to 98 wt. % and 95 to 98 wt. %; or can be equal to any disclosed value, optionally at ±5 percentage points.

The mineralising composition can contain 2 to 70 wt. % lactic acid microorganism, and the preferred upper limits and lower limits of this interval can be: 20 wt. % and 30 wt. %. Thus, the quantity of the lactic acid microorganism can preferably be comprised in any interval having the upper and lower limits mentioned above, in particular: 2 to 20 wt. % and 30 to 70 wt. %; or can be equal to any disclosed value, optionally at ±5 percentage points.

The mineralising composition can contain 25 to 70 wt. % nutritive substance, and the preferred upper limits and lower limits of this interval can be: 30 wt. % and 50 wt. %. Thus, the quantity of the nutritive substance can preferably be comprised in any interval having the upper and lower limits mentioned above, in particular: 25 to 50 wt. % and 30 to 70 wt. %; or can be equal to any disclosed value, optionally at ±5 percentage points.

All the possible combinations of the various intervals disclosed above are possible, including:
- 80 to 98 wt. % or 30 to 70 wt. % living structure and 2 to 20 wt. % lactic acid microorganism;
- 30 to 70 wt. % lactic acid microorganism and 25 to 50 wt. % nutritive substance; and
- 2 to 20 wt. % lactic acid microorganism and 30 to 70 wt. % nutritive substance.

The mineral composition is advantageously formulated in such a way as to enable extemporaneous use. It can undergo milling and/or dilution in order to promote its use and be ready to use.

Mineral Substance

A mineral substance according to the invention and obtainable from the method previously described is described below.

Such a mineral substance comprises:
a. a living structure;
b. mineral matter synthesised by the living structure; and
c. at least one lactic acid microorganism.

The quantity of living structure can be in the same intervals as described above for the mineralising composition.

The quantity of lactic acid microorganism can be in the same intervals as described above for the mineralising composition.

Preferably, the mineral substance comprises 25 to 70 wt. % the mineral matter, and the preferred upper limits and lower limits of this interval can be: 30 wt. %, 40 wt. %, 50 wt. % and 60 wt. %. Thus, the quantity of the mineral matter can preferably be comprised in any interval having the upper and lower limits mentioned above, in particular: 30 to 70 wt. %, 30 to 60 wt. %, 40 to 60 wt. % and approximately 50 wt. %; or can be equal to any disclosed value, optionally at ±5 percentage points.

The quantity of nutritive substance can be in the same intervals as described above for the mineralising composition.

All the combinations mentioned above for the mineral composition are also valid for the mineral substance.

The mineral substance can also comprise a base substrate suitable for the proliferation of the living structure or of the lactic acid microorganism.

The mineral substance can be active or inactive.

The mineral substance can be in solid form, such as a paste-like, gelled, powdery or granular (amorphous, crystallised or a mixture of the two) form. The mineral substance can be in fluid form, such as in liquid or gas form, capable of solidifying or being condensed into a solid in particular through crystallisation in a porous and/or loose medium such as soil.

The mineral substance can also comprise at least one salt such as a salt chosen from the group consisting of magnesium oxide (MgO), magnesium sulphate ($MgSO_4$), phosphate ($H_3PO_4$), calcium chloride ($CaCl_2$), barium chloride ($BaCl_2$), sodium fluorosilicate ($Na_2SiF_6$), carbonate salt ($CO_3^{2-}$), sodium silicate ($Na_2SiO_3$) and mixtures thereof. The salt is advantageously in anhydrous form.

Advantageously, the mineral substance comprises 25 to 50 wt. % of the salt, and the preferred upper limits and lower limits of this interval can be: 30 wt. %, 40 wt. % and 45 wt. %. Thus, the quantity of salt can preferably be comprised in any interval having the upper and lower limits mentioned above, in particular: 25 to 50 wt. % and 40 to 50 wt. %; or can be equal to any disclosed value, optionally at ±5 percentage points.

The mineral substance can also comprise a cohesion and/or texturing agent.

Advantageously, the mineral substance comprises 25 to 50 wt. % cohesion and/or texturing agent, and the preferred upper limits and lower limits of this interval can be: 30 wt. %, 40 wt. % and 45 wt. %. Thus, the quantity of cohesion and/or texturing agent can preferably be comprised in any interval having the upper and lower limits mentioned above, in particular: 30 to 50 wt. %; or can be equal to any disclosed value, optionally at ±5 percentage points.

The exact composition of the mineral substance is chosen according to the mineral substrate on which it is intended to be applied. Thus, the material of artificial building surfaces damaged by time could thus be reconstituted according to their crystallographic nature. The recreation of the "patina" of this material would thus be facilitated.

The living structure, the lactic acid microorganism, the nutritive substance and the cohesion and/or texturing agent are as described above.

The mineral substance is advantageously formulated in such a way as to enable extemporaneous use.

The mineral substance can be obtained from a composition comprising at least the living structure and the lactic acid microorganism. Nutritive substances for the living structure and/or the lactic acid microorganism are preferably comprised in the composition. The composition can be in the form of a liquid that is more or less viscous or a solid (for example in the form of granules or a powder).

The mineral matter, and optionally the base substrate, of the mineral substance are preferably present in a porous form, with pores opening outside of the mineral substance. In other words, the porous volume is in fluid contact with the outside environment. This porous volume constitutes a space in which the living structure and the lactic acid microorganism are present, in particular in the deactivated state.

Use

The mineral substance described above can be used as a filler, additive or hydraulic binder in a mixture for filling, resurfacing, cementing, assembling, priming, coating, etc. For example, such a mixture comprising the mineral substance can be used to fill a cavity caused by erosion in limestone.

Thus, the mineral substance can also be used for immobilising waste and/or sediments of all kinds, the restructuring of structures, the regeneration of mortar and concrete by filling the cracks, the reinforcement of porous and/or unstable loose soils, the creation of mineralisations for curative, preventive or decorative purposes.

The immobilisation of waste means the possibility of containing or confining it in a mixture made from the mineral substance obtained by this method.

More generally, the present invention relates to the use of a combination of a living structure and a lactic acid microorganism in symbiosis with each other as a mineralisation agent, in particular in a construction material, for example a self-regenerating material.

EXAMPLES

Example 1

This example relates to the recycling of construction materials, the construction material forming a base substrate. The construction material, for example Portland mortar, or the portion of the latter is previously crushed into fragments that are advantageously centimetric.

In this method, the living structure, the lactic acid microorganism and the nutritive substance are provided together in the form of an aqueous bath rich in lactic acid microorganism.

The base substrate is then brought in contact with this aqueous bath thus enabling leaching of the surfaces of the base substrate through the action of the lactic acid produced by the lactic acid microorganism which progressively disintegrates the base substrate at the surface, freeing silico-carbonate substances.

In other words, the superficial layers of the construction material or of the portion thereof are dissolved by a pickling effect and leads to the destruction of their crystalline structure. Moreover, the leaching has a cleaning effect on the surfaces of the base substrate which is favourable to the later mineralisation-carbonation which enables an additional cleaning step, in particular via destructive or dangerous chemical methods, to be avoided.

The lactic acid microorganism was previously cultivated until it reached its exponential growth phase. The culture time necessary for reaching this stage is generally between 48 and 72 hours at a temperature of 20° C. for a volume of 5 L of Sabouraud agar.

Together with the leaching, the method can include the salting-out of the surfaces of the base substrate, thus ensuring progressive leaching of these surfaces. Flowing of the leaching mixture can be carried out from several days to several months. The flowing is preferably carried out using a lift and force pump enabling the leaching bath to be set in motion.

Then, a living structure is provided for the mineralisation, which enables a material comprising mineral matter synthesised by the living structure, optionally in a mixture with other mineral matter not synthesised by the living structure, to be obtained.

Figure 2:
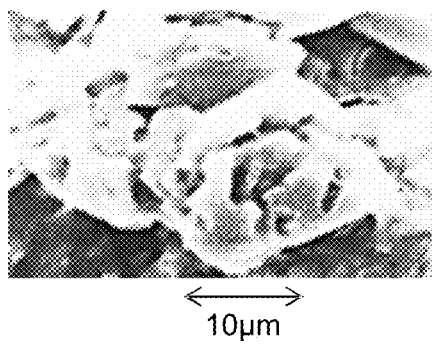
FIG. 2 is a black-and-white photograph showing mineral matter, in the form of labyrinth-like neo-crystals of calcite, obtainable through the present invention.

Thus, it is possible to reuse these construction materials otherwise destined to be destructed or to be dumped. The appearance of the mineral matter obtained from a Portland mortar is shown in FIG. 2 in which the following are visible:
 a. the mineral matter 1, here silico-carbonate matter;
 b. the base substrate 2; and
 c. the solution rich in living structure and lactic acid microorganism 3.

Example 2

This example relates to the treatment of a cracked construction material (filling), in particular cracked mortar. This cracked mortar thus forms the base substrate.

In this example, the lactic acid microorganism (here a lactic acid bacterium) and the nutritive substance are provided together in the form of an aqueous solution rich in lactic acid microorganism in its exponential growth phase.

The base substrate is brought in contact with the aqueous solution enabling prior cleaning of the wall of the cracks. The contact is created by applying the aqueous solution with a brush or a sprayer.

The cleaning action is quick, and after few hours (1 to 2 hours), the living structure is provided and brought in contact with the base substrate by dripping a urea culture medium comprising, in a volume of one litre, 1 g of glucose, 10 g of urea, 10 g of glycerol carbonate, and the mineralising living structure such as *Bacillus megaterium* and/or *Bacillus cereus* (calcifying bacteria) in their exponential growth phase.

The living structure enables the progressive remineralisation of the cracks.

The interest of the symbiosis is based here on the use of a lactic acid bacterium, the main role of which is to clean the walls of the cracks to be remineralised through secretion of lactic acid, and jointly the use of calcifying bacteria for filling the cracks.

Figure 3:
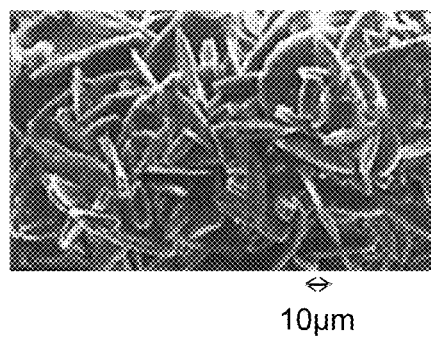
FIGS. 3 and 4 are photographs showing varieties of mineral matter, in the form of crystalline biocarbonates, obtainable through the present invention.
Figure 4:
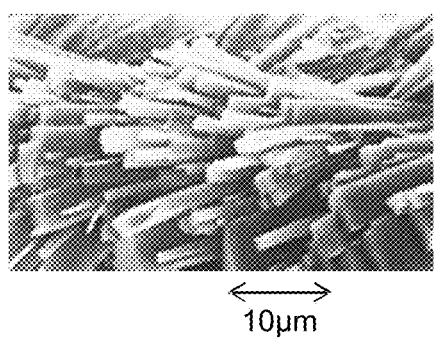
Figure 5:
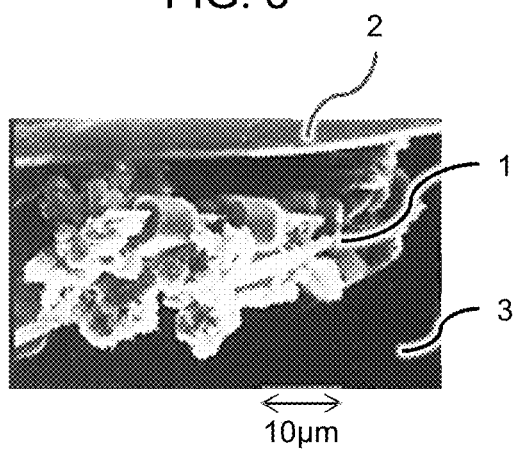
FIG. 5 is a black-and-white photograph of a silico-carbonate mineral product obtained through the implementation of the method according to example 1.
Figure 6:
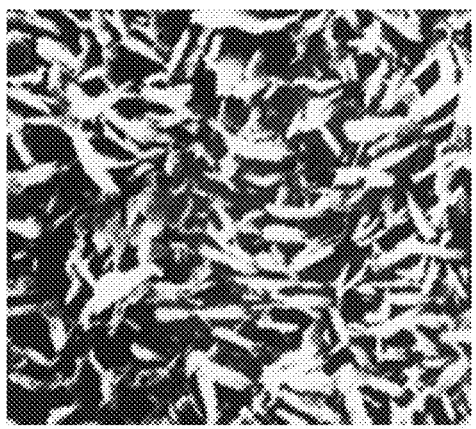
FIG. 6 is a photograph showing silico-carbonate mineral matter obtainable through the present invention.
Figure 7:
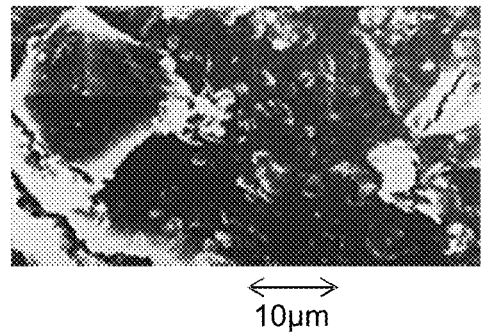
FIGS. 7 and 8 are photographs showing types of mineral matter in the form of a crystalline deposit of calcium oxalate obtainable through the present invention.
Figure 8:
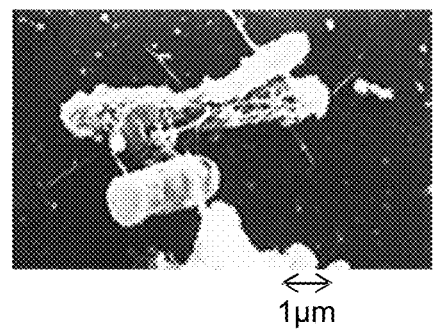
Figure 9:
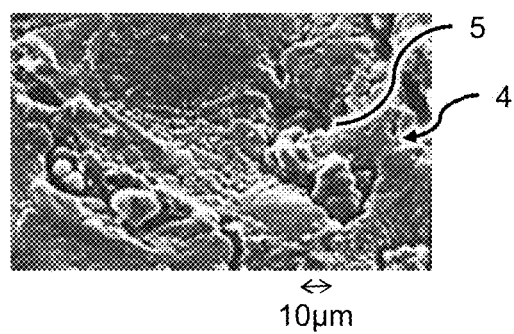
FIG. 9 is a black-and-white photograph of the filling of cracks in mortar according to the implementation of the method according to example 2.

At the end of the method, the filling of the cracks by varied biomineral products, in particular calcic and oxalic biomineral products, is observable in FIG. 3. In which the following can be seen:
 a. the cracked base substrate 4; and
 b. the mineral matter (calcic and oxalic) 5.

Contrary to a mere filling, which always leaves a discontinuous interface between the material to be repaired and the fill, here the reparation of the material is stronger because the leaching produced by the lactic acid microorganism enables better anchoring of the mineral matter synthesised by the lactic acid microorganism in such a way that there is close continuity between the material and the mineral matter.

Thus, on artificial surfaces, for example such as those of buildings made of natural stone and/or mortar and/or concrete of any type, various biocrystalline coatings are created in this way: carbonates, oxalates, sulphates (desert rose), phosphates (apatite), fluosilicate and new hybrid materials are created that are both organic and mineral at molecular scale.

Example 3

This example relates to the treatment of products of coral, calcareous algae, shells, hereinafter called fresh marine shell products. These fresh marine shell products are used as a base substrate. The microorganism, the living structure and the nutritive substance are provided together in the form of an aqueous solution rich in lactic acid microorganism in its exponential growth phase.

The base substrate is subjected to leaching by being brought in contact with the aqueous solution. The base substrate then undergoes enzymatic fermentation that is antiseptic and acts on the organic/inorganic bonds of the composition of the natural biocrystalline structures comprised in the base substrate.

This preparatory step makes the base substrate more suitable for the artificial petrification during the following steps of the method.

This method, which also involves deodorising the obtained carbonate mineral matter, enables:
 a. the recycling of the fresh marine shell products to be improved; and
 b. the artificial surfaces to be cleaned in the context of their renovation/remineralisation.

The method further involves the treatment of artificial surfaces using the obtained mineral substance. This treatment is simple and has a low cost in a field in which fouling often requires the use of destructive abrasives. Finally, the method involves the remineralisation of the organic and mineral deposits caused by the pollution carried out by the living structure. It thus allows time to be saved during renovation/repair operations. Isolated objects such as rubble stones, blocks of stone of any mineralogical nature or construction materials such as brick, tile, concrete, cement or objects that can be taken apart such as statues can be subjected to this method.

Example 4

This example relates to the treatment of homogenate and bushes. Samples of crushed material from bushes are used as a base substrate and are immersed in an aqueous bath rich in lactic acid microorganism in its exponential growth phase and comprising a nutritive substance. These samples undergo enzymatic fermentation that partly digests the cellulosic, pecto-cellulosic and ligneous fibres.

This method is aimed in particular at the industries of the wood sector faced with the necessity of destroying cellulosic, pecto-cellulosic and ligneous fibres while rapidly enabling the digestion thereof.

For example, a sampling of bush crushed material of several litres treated according to the method of the present invention through immersion during at least 72 hours and at most 144 hours at a temperature of 20° C. enabled, through predigestion of the fibres of the bush crushed material, once dried, easier petrification under the action of the living structure in comparison with the methods described in FR 2723080 and EP 0708836.

Example 5

This example relates to soil induration. Loose alluvial type soil profiles reformed into cylinders having a diameter of 4 centimetres and a height of 10 centimetres are used as a base substrate and are first percolated with an aqueous solution rich in lactic acid microorganism in its exponential growth phase and comprising a nutritive substance.

The method according to the invention enables the preparation of the sediment with maximum petrification due to the essential action of enzymatic release carried out by the lactic acid microorganism over 72 hours.

The reformed loose alluvial type soil profiles are then infiltrated with a nutritive solution consisting of glucose, urea and glycerol carbonate containing the living structure, in particular *Bacillus megaterium* and/or *Bacillus cereus* in their exponential growth phase. The simplified nutritive medium consists of 5 g of peptone, 10 g of glucose, 0.005 g of $MgSO_4$, 0.1 g of $MgCO_3$, 0.1 g of $K_2CO_3$, 0.1 g of $Ca(NO_3)_2$, 0.05 g of $ZnSO_4$ and water in quantities sufficient for one litre.

With this method, progressive induration of the sediment is observed, through development of crystalline sedimentation around the alluvial grains from as early as the first days of the treatment carried out, in total, for a week and resulting in a solid sandstone formation after about fifteen days of natural drying of the specimens.

The conventional mineralisation by the living structure of the prior art is reinforced in this example by the mineralisation caused by the organic carbonatation resulting from the activity of the lactic acid microorganism that produces carbon dioxide, from this carbon dioxide, urea and glycerol carbonate.

Through microscopic examination, it is noted that the progressive induration observed experimentally results from the coalescing of the mineral matter synthesised by the living structure in which the latter and the lactic acid microorganism are dormant but can be revived. The biominerals have in particular a specific morphoscopic and endoscopic appearance called labyrinth-like, that is to say, that they are both porous and in fluid communication with the outside environment enabling various exchanges (gaseous, liquid, living) to take place and form a habitat for the living structure and the microorganism in the dormant state.

The mucoprotein silico-carbonate substances essential components of the biological gluing of the mineral matter secreted by the living structure in crystalline form participate in the encapsulation of the living structure and of the lactic acid microorganism clearly promoted by the glycerol carbonate and/or derivatives that boost the integration of the organic carbon of the bonded, recombinant, hidden mucoproteins and of biological glues in general.

The invention claimed is:

1. A mineral cement repairing substance comprising:
   25 to 73 wt. % of a living structure or at least a portion thereof;
   2 to 50 wt. % of at least one lactic acid microorganism;
   25 to 70 wt. % of mineral matter synthesised by the living structure or the portion thereof; and
   a nutritive substance,
   wherein the at least one lactic acid microorganism is chosen from the group consisting of:
      the family Aerococcaceae,
      the family Bifidobacteriaceae,
      the family Carnobacteriaceae,
      the family Enterococcaceae,
      the family Lactobacillaceae,
      the family Leuconostocaceae,
      the family Saccharomycetaceae,
      the family Sporolactobacillaceae, and
      the family Streptococcaceae,
   wherein the living structure is a calcifying bacteria chosen from the genera Bacillus and Pseudomonas,
   wherein the nutritive substance is chosen from the group consisting of:
      an aqueous mixture comprising 5 g of glucose and 10 g of fructose, in 1 L of distilled water, and
      de Man, Rogosa and Sharpe agar (M.R.S. agar), and
   wherein the lactic acid microorganism accelerates production of the mineral matter by the living structure.

2. The mineral cement repairing substance according to claim 1, further comprising a base substrate suitable for proliferation of the living structure and/or of the lactic acid microorganism.

3. The mineral cement repairing substance according to claim 1, wherein the mineral matter, and optionally a base substrate, is present in a porous form, with pores, opening outside of the mineral cement repairing substance, in which the living structure and the lactic acid microorganism are present.

4. A mineralising cement repairing composition comprising:
   25 to 73 wt. % of a living structure or at least a portion of a living structure;
   2 to 50 wt. % of at least one lactic acid microorganism; and
   25 to 70 wt. % of a nutritive substance,
   wherein the at least one lactic acid microorganism is chosen from the group consisting of:
      the family Aerococcaceae,
      the family Bifidobacteriaceae,
      the family Carnobacteriaceae,
      the family Enterococcaceae,
      the family Lactobacillaceae,
      the family Leuconostocaceae,
      the family Saccharomycetaceae,
      the family Sporolactobacillaceae, and
      the family Streptococcaceae,
   wherein the living structure is a calcifying bacteria chosen from the genera *Bacillus* and *Pseudomonas*, wherein the nutritive substance is chosen from the group consisting of:
an aqueous mixture comprising 5 g of glucose and 10 g of fructose, in 1 L of distilled water, and
de Man, Rogosa and Sharpe agar (M.R.S. agar), and
wherein the lactic acid microorganism accelerates production of a mineral matter by the living structure.

5. The mineral cement repairing substance according to claim 2, wherein the base substrate is chosen from the group consisting of stone, a portion of an existing edifice, or a construction material.

6. The mineralising cement repairing composition according to claim 4, further comprising a base substrate suitable for proliferation of the living structure and/or of the lactic acid microorganism.

7. The mineralising cement repairing composition according to claim 4, wherein the mineral matter, and optionally a base substrate, is present in a porous form, with pores opening outside of the mineralising cement repairing composition, in which the living structure and the lactic acid microorganism are present.

8. The mineralising cement repairing composition according to claim 6, wherein the base substrate is chosen from the group consisting of stone, a portion of an existing edifice, or a construction material.

* * * * *